US008122884B2

(12) United States Patent
Daly et al.

(10) Patent No.: US 8,122,884 B2
(45) Date of Patent: *Feb. 28, 2012

(54) DOUBLE-ENDED BLOWER AND VOLUTES THEREFOR

(75) Inventors: Geoffrey Daniel Daly, Paddington (AU); Alexander Virr, Balmain (AU); Stephen Anthony Lea, Winston Hills (AU); Dion Charles Chewe Martin, Concord (AU); Nicholas Jerome Reed, Mount Colah (AU); Larry Puckeridge, Marrickville (AU); Timothy Tsun-Fai Fu, Carlingford (AU)

(73) Assignee: ResMed Limited, Bella Vista, New South Wales (AU)

( * ) Notice: Subject to any disclaimer, the term of this patent is extended or adjusted under 35 U.S.C. 154(b) by 693 days.

This patent is subject to a terminal disclaimer.

(21) Appl. No.: 11/135,477

(22) Filed: May 24, 2005

(65) Prior Publication Data
US 2005/0217673 A1 Oct. 6, 2005

Related U.S. Application Data

(63) Continuation of application No. 10/360,757, filed on Dec. 10, 2001, now Pat. No. 6,910,483.

(51) Int. Cl.
| | |
|---|---|
| *A61M 16/00* | (2006.01) |
| *A62B 7/00* | (2006.01) |
| *A62B 7/04* | (2006.01) |
| *F16K 31/02* | (2006.01) |
| *F16K 31/26* | (2006.01) |
| *F01D 3/02* | (2006.01) |
| *F04B 17/00* | (2006.01) |
| *F04B 35/00* | (2006.01) |

(52) U.S. Cl. ......... 128/204.26; 128/204.18; 128/204.23; 415/98; 415/100; 417/350

(58) Field of Classification Search ............. 128/204.18, 128/204.21, 204.23, 204.26, 205.11, 205.24; 415/101–103, 93, 94, 204–206, 211.1, 211.2, 415/208.2, 208.3, 13, 14; 417/423.1, 350, 417/244, 199.1, 211.2, 214.1, 212.1, 119, 417/177, 185, 198 R, 198 A, 423.5, 423.15, 417/423.14, 120, 124, 157 R, 199
See application file for complete search history.

(56) References Cited

U.S. PATENT DOCUMENTS

RE19,826 E * 1/1936 Aisenstein ................... 415/108
(Continued)

FOREIGN PATENT DOCUMENTS

DE 275612 1/1913
(Continued)

OTHER PUBLICATIONS

International Search Report for PCT/AU2004/000771, Mailed Aug. 23, 2004, 6 pages.
(Continued)

*Primary Examiner* — Kristen Matter
(74) *Attorney, Agent, or Firm* — Nixon & Vanderhye, P.C.

(57) ABSTRACT

A double-ended variable speed blower for Continuous Positive Airway Pressure (CPAP) ventilation of patients includes two impellers in the gas flow path that cooperatively pressurize gas to desired pressure and flow characteristics. Thus, the double-ended blower can provide faster pressure response and desired flow characteristics over a narrower range of motor speeds, resulting in greater reliability and less acoustic noise.

43 Claims, 10 Drawing Sheets

U.S. PATENT DOCUMENTS

| | | | |
|---|---|---|---|
| 2,220,669 A | | 11/1940 | Allen |
| 2,945,619 A | | 7/1960 | Ballard |
| 3,620,638 A | * | 11/1971 | Kaye et al. .................... 415/146 |
| 4,037,994 A | | 7/1977 | Bird |
| 4,105,372 A | * | 8/1978 | Mishina et al. ............... 417/243 |
| 4,171,190 A | * | 10/1979 | Hudson .......................... 417/350 |
| 4,229,142 A | * | 10/1980 | Le Dall et al. .................. 417/38 |
| 4,523,896 A | | 6/1985 | Lhenry et al. |
| 4,576,616 A | | 3/1986 | Mottram et al. |
| 4,802,819 A | * | 2/1989 | Bevington et al. ......... 415/199.3 |
| 4,946,348 A | | 8/1990 | Yapp |
| 4,969,803 A | * | 11/1990 | Turanskyj .................... 417/247 |
| 5,127,800 A | | 7/1992 | Hyll et al. |
| 5,391,063 A | * | 2/1995 | Hantle et al. ............... 417/423.7 |
| 5,888,053 A | | 3/1999 | Kobayashi et al. |
| 6,109,865 A | * | 8/2000 | Ishikawa ......................... 415/98 |
| 6,158,978 A | * | 12/2000 | Norbury, Jr. ................. 417/350 |
| 6,210,116 B1 | * | 4/2001 | Kuczaj et al. ................. 416/185 |
| 6,213,119 B1 | | 4/2001 | Brydon et al. |
| 6,216,691 B1 | | 4/2001 | Kenyon et al. |
| 6,257,171 B1 | | 7/2001 | Rivard |
| 6,340,288 B1 | | 1/2002 | Hulkkonen et al. |
| 6,349,724 B1 | | 2/2002 | Burton et al. |
| 6,397,841 B1 | | 6/2002 | Kenyon et al. |
| 6,471,493 B2 | * | 10/2002 | Choi et al. .................... 417/350 |
| 6,514,053 B2 | | 2/2003 | Takura et al. |
| 6,622,724 B1 | | 9/2003 | Truitt et al. |
| 6,837,260 B1 | | 1/2005 | Kuehn |
| 6,896,478 B2 | | 5/2005 | Botros et al. |
| 6,910,483 B2 | | 6/2005 | Daly et al. |
| 2002/0056453 A1 | | 5/2002 | Klopp et al. |
| 2002/0159897 A1 | * | 10/2002 | Kegg et al. .................... 417/368 |
| 2003/0084900 A1 | | 5/2003 | Leclerc et al. |
| 2003/0168064 A1 | | 9/2003 | Daly et al. |
| 2005/0005937 A1 | | 1/2005 | Farrugia et al. |
| 2005/0103339 A1 | | 5/2005 | Daly et al. |
| 2007/0036662 A1 | | 2/2007 | Pesola et al. |

FOREIGN PATENT DOCUMENTS

| | | |
|---|---|---|
| DE | 30 05 094 | 8/1981 |
| EP | 1318307 | 6/2003 |
| WO | WO 98/31937 | 7/1998 |
| WO | WO 98/33433 | 8/1998 |
| WO | 99/64747 | 3/1999 |
| WO | WO 99/13932 | 3/1999 |
| WO | WO 99/22794 | 5/1999 |
| WO | 00/42324 A2 | 7/2000 |
| WO | WO 00/42324 | 7/2000 |

OTHER PUBLICATIONS

J.H. Emerson Co., Cough Assist, "Non-Invasive Removal of Bronchial Secretions," 2 pages.

European Search Report for co-pending European Application No. 08 15 7382, mailed Oct. 13, 2008, 6 pages.

European Search Report for co-pending European Application No. 10 1802132, mailed Dec. 13, 2010, 7 pages.

Notification of the First Office Action from State Intellectual Property Office of the People's Republica of China for Application No. 200910001413.0 dated Dec. 16, 2010 (19 pages).

* cited by examiner

DOUBLE-ENDED BLOWER AND VOLUTES THEREFOR

CROSS REFERENCE TO RELATED APPLICATION

This is a continuation of U.S. application Ser. No. 10/360,757, filed Dec. 10, 2001, now U.S. Pat. No. 6,910,483 B2, incorporated herein by reference in its entirety.

1. FIELD OF THE INVENTION

The present invention relates to an apparatus for supplying breathable gas to a human, used in, for example, Continuous Positive Airway Pressure (CPAP) treatment of Obstructive Sleep Apnea (OSA), other respiratory diseases and disorders such as emphysema, or the application of assisted ventilation.

2. DESCRIPTION OF RELATED ART

CPAP treatment of OSA, a form of Noninvasive Positive Pressure Ventilation (NIPPV), involves the delivery of a pressurized breathable gas, usually air, to a patient's airways using a conduit and mask. Gas pressures employed for CPAP can range from 4 cm $H_2O$ to 28 cm $H_2O$, at flow rates of up to 180 L/min (measured at the mask), depending on patient requirements. The pressurized gas acts as a pneumatic splint for the patient's airway, preventing airway collapse, especially during the inspiratory phase of respiration.

Typically, the pressure at which a patient is ventilated during CPAP is varied according to the phase of the patient's breathing cycle. For example, the ventilation apparatus may be pre-set to deliver two pressures, an inspiratory positive airway pressure (IPAP) during the inspiration phase of the respiratory cycle, and an expiratory positive airway pressure (EPAP) during the expiration phase of the respiratory cycle. An ideal system for CPAP is able to switch between IPAP and EPAP pressures quickly, efficiently, and quietly, while providing maximum pressure support to the patient during the early part of the inspiratory phase.

In a traditional CPAP system, the air supply to the patient is pressurized by a blower having a single impeller. The impeller is enclosed in a volute, or housing, in which the entering gas is trapped while pressurized by the spinning impeller. The pressurized gas gradually leaves the volute and travels to the patient's mask.

There are currently two common ways in which the blower and impeller can be configured to produce the two different pressures, IPAP and EPAP, that are required in an ideal CPAP system. A first method is to set the motor/impeller to produce a constant high pressure and then employ a diverter valve arrangement that modulates the high pressure to achieve the required IPAP and EPAP pressures. CPAP systems according to the first method are called single-speed bi-level systems with diverters. A second method is to accelerate the motor that drives the impeller to directly produce IPAP and EPAP pressures. CPAP systems according to the second method are called variable-speed bi-level systems.

Variable-speed bi-level CPAP systems have a number of particular disadvantages. A first disadvantage is that in order to switch rapidly between IPAP and EPAP, the impeller must be accelerated and decelerated rapidly. This causes excessive stress on the impeller, motor, and bearings. However, if the impeller is accelerated slowly, the pressure rise may be unsatisfactorily slow, and thus, the patient may not receive adequate treatment.

Rapid acceleration and deceleration of the motor and impeller also result in excessive heat generation and undesirable acoustic noise. ("Undesirable" acoustic noise, as the term is used here, refers to acoustic noise that is overly loud, as well as acoustic noise which occurs at a frequency that is irritating to the user, regardless of its volume.) In addition, design engineers are often forced to make a compromise, sacrificing optimal pressure and flow characteristics in favor of achieving a desired peak pressure.

3. SUMMARY OF THE INVENTION

The present invention, in one aspect, relates to variable speed blowers providing faster pressure rise time with increased reliability and less acoustic noise. Blowers according to the present invention comprise a gas flow path between a gas inlet and a gas outlet, a motor, and an impeller assembly.

Preferably, the impeller assembly may include a shaft in communication with the motor for rotational motion about a first axis and first and second impellers coupled, e.g., fixedly secured, to the shaft. The impellers are placed in fluid communication with one another by the gas flow path such that both impellers are disposed between the gas inlet and the gas outlet to cooperatively pressurize gas flowing from the gas inlet to the gas outlet.

In one embodiment, the impellers are disposed in series between the gas inlet and the gas outlet. The blower may also comprise a housing, portions of the housing being disposed around each of the first and second impellers. In particular, the housing may include first and second volutes, the first volute containing gas flow around the first impeller and the second volute containing gas flow around the second impeller. The gas inlet may be located in the first volute and the gas outlet may be located in the second volute.

The impellers may be arranged such that they are vertically spaced from one another along the first axis. In particular, they may be disposed at opposite ends, respectively, of the blower housing.

A blower according to the present invention may have varying configurations. In one embodiment, the two impellers are designed to rotate in the same direction. In another embodiment, the two impellers are designed to rotate in opposite directions.

Another aspect of the invention relates to an in-plane transitional scroll volute for use in either a double- or single-ended blower. The in-plane transitional scroll volute gradually directs pressurized air away from a spinning impeller.

These and other aspects of the present invention will be described in or apparent from the following detailed description of preferred embodiments.

4. BRIEF DESCRIPTION OF THE DRAWINGS

Various exemplary embodiments will be described with reference to the following drawings, in which like reference characters represent like features, wherein:

FIG. 1a schematically illustrates a CPAP/NIPPV apparatus according to one embodiment of the present invention.

5. DETAILED DESCRIPTION

Figure 1:
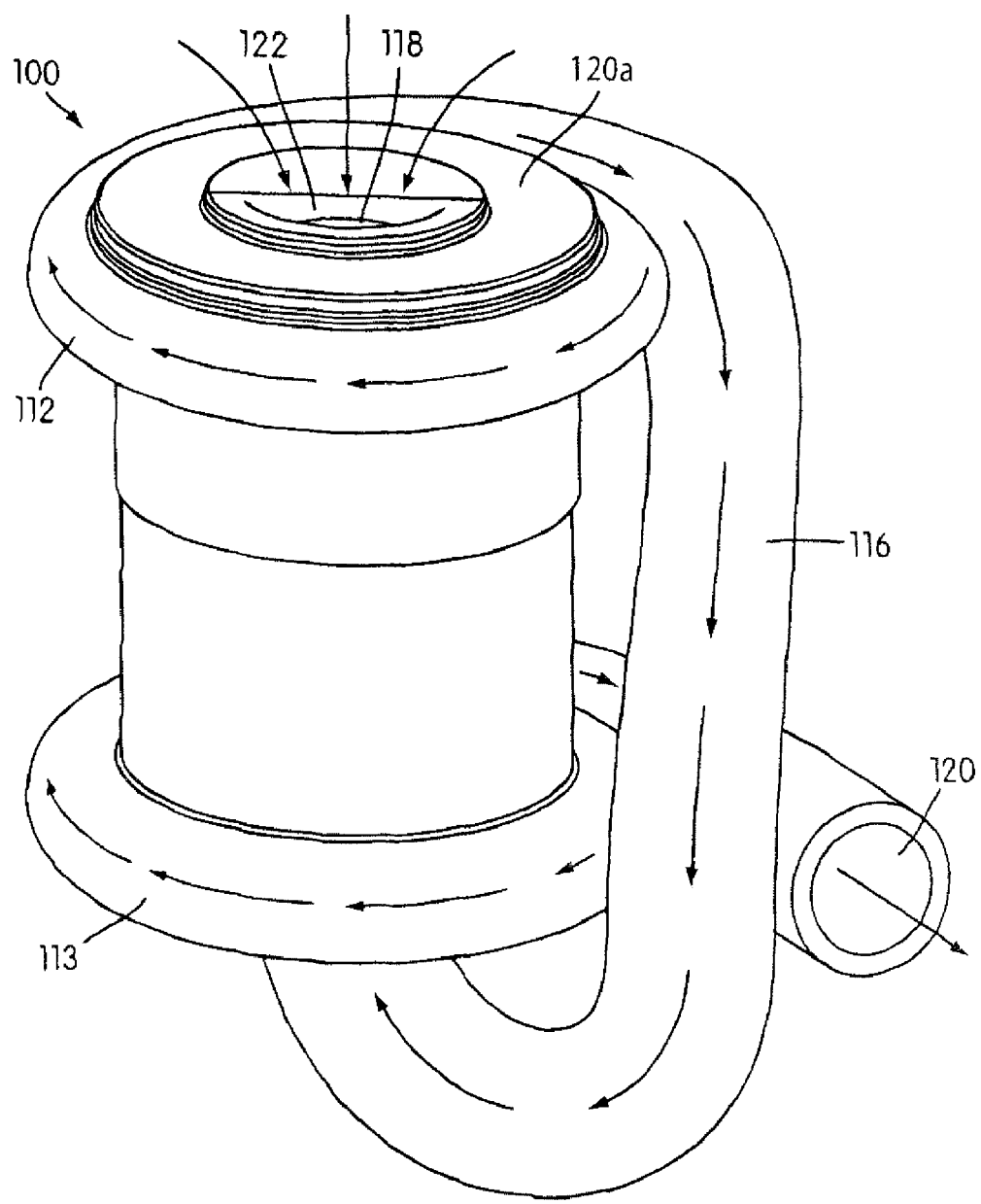
FIG. 1 is a perspective view of a double-ended blower according to a first embodiment of the present invention.
Figure 1A:
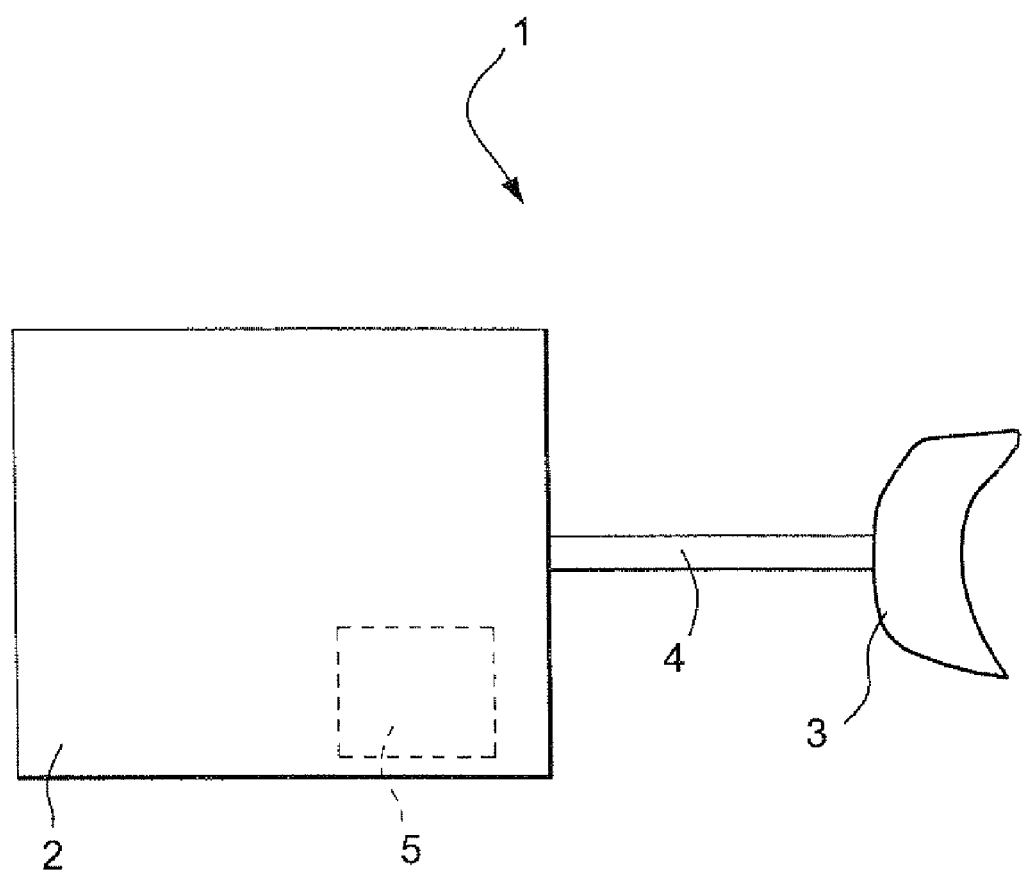

FIG. 1a schematically illustrates a CPAP/NIPPV apparatus 1 according to a sample embodiment of the present invention. Apparatus 1 includes a flow generator 2, a patient interface 3 in the form of a mask, and an air delivery tube 4 fluidly coupling the flow generator 2 and the patient interface. The flow generator includes a blower 5, as described in more detail herein.

Referring now to the Figures, FIG. 1 is a perspective view of a double-ended blower 100 according to a first embodiment of the present invention. Blower 100 has a generally cylindrical shape with impeller housings, or volutes 112, 113, disposed at each end. Thus, blower 100 accommodates two impellers 114, 115, which are best seen in the cut-away perspective view of FIG. 2.

Figure 2:
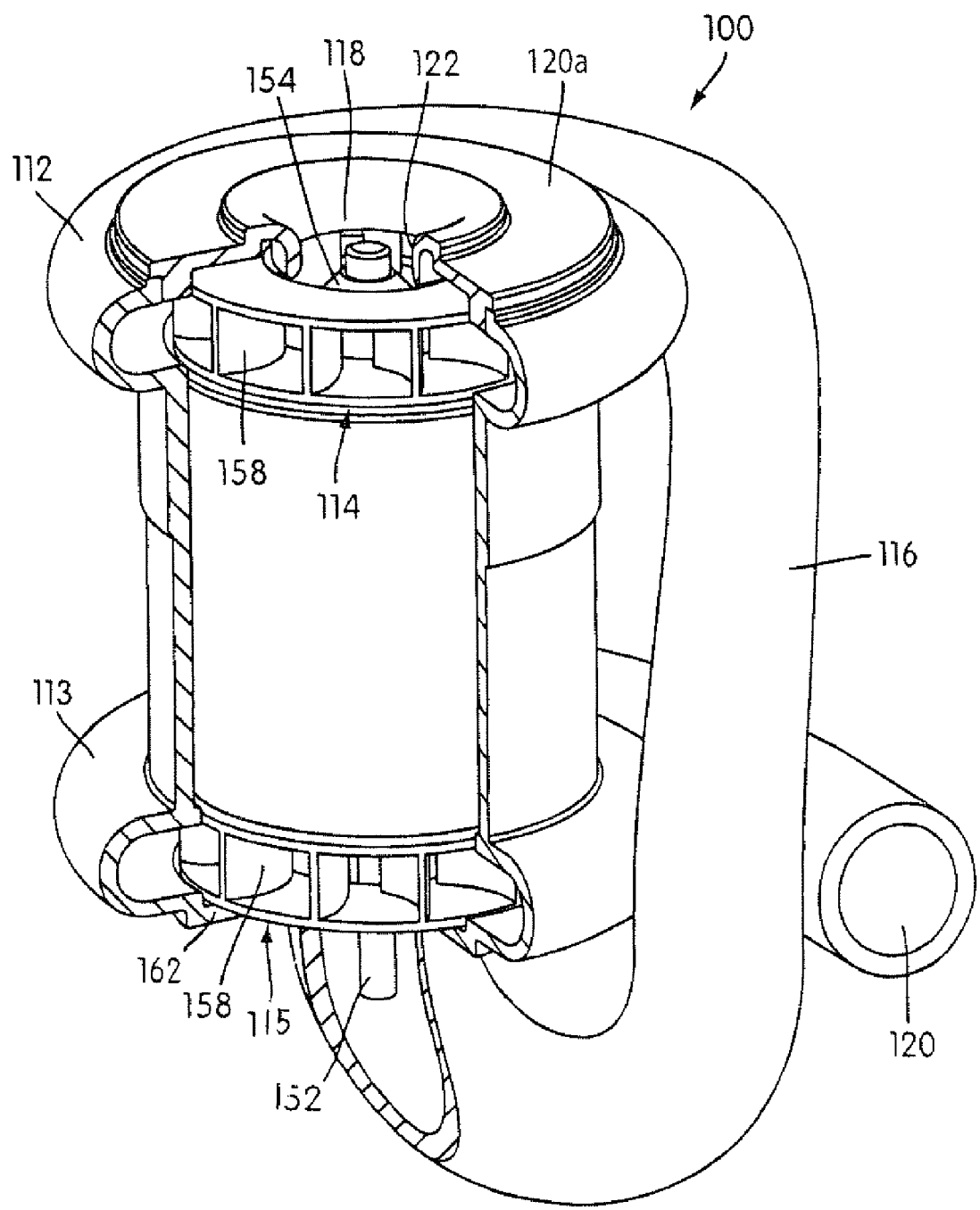
FIG. 2 is a partially sectional perspective view of the double-ended blower of FIG. 1.

Referring to FIGS. 1 and 2, the two impellers 114, 115 are placed in fluid communication with one another by an airpath 116. The airpath 116 of blower 100 is comprised of piping that extends from the first volute 112 to the second volute 113, the terminal ends of the airpath 116 being contoured around, and gradually fusing with, the body of blower 100 proximate to the volutes 112, 113 to form a single, integral structure. The airpath 116 may be comprised of rigid piping that is integrally molded with the other components of the blower 100, or it may be comprised of flexible piping (e.g., metallic or plastic flexible piping).

Blower 100 has a single air intake 118 positioned such that air, or another suitable gas, flows directly into the first volute 112 and can be drawn in by the turning impeller 114 inside the first volute 112. Once drawn into the air intake 118, the air is circulated and pressurized by the motion of the impeller 114 before gradually exiting the volute 112 and entering the airpath 116. Once in the airpath 116, the air travels to the second volute 113, where it is further circulated and pressurized by the impeller 115 of the second volute 113 before exiting the blower 100 through the outflow conduit 120. The path of the air in blower 100 is indicated by the arrows in FIG. 1. As shown, in blower 100, air from the first volute 112 travels along a relatively straight section of the airpath 116 and enters the second volute 113 through an intake cavity just above the second volute 113 (not shown in FIG. 1).

Blower 100 could have two air intakes 118, one for each volute 112, 113, if the impellers 114, 115 are designed to work in parallel, rather than in series. This type of parallel impeller arrangement may be beneficial if installed in a low-pressure CPAP device requiring high flow rates. However, other means for generating high flow rates in a low-pressure CPAP device are known in the art.

The design of the airpath 116 can effect the overall performance of the blower 100. In general, several design considerations influence the design of an airpath for use in blowers according to the present invention. First, airpaths to be used in blowers according to the present invention are most advantageously configured to provide low flow resistance, because low flow resistance in the airpath minimizes the pressure drop between the two volutes 112, 113 in the blower. Second, airpath are best configured such that the air entering the second volute 113 enters from a direction for which the blades of the impeller 115 were designed. (As will be described in more detail below, the two impellers of a blower according to the present invention may be designed to spin in the same or different directions.) Finally, airpaths for blowers according to the present invention are most advantageously of a compact design.

The design considerations set forth above are best embodied in an airpath having long, sweeping bends to minimize the pressure drop around the bends. It is also beneficial to have a relatively straight section after a bend in the airpath, because a relatively straight section after a bend allows the gas flow to become more fully developed before entering a volute. An appropriate length for a straight airpath section following a bend is about three times the diameter of the airpath. The relatively straight section also ensures that the flow entering the second volute 113 is axial, the flow orientation for which many impellers are designed. If additional flow shaping is desired, stator vanes or other similar flow directing structures may be added to the blower, however, stator vanes may be costly in terms of flow impedance and pressure drops.

In view of the three major airpath design considerations set forth above, the airpath 116 of the embodiment depicted in FIG. 1 has a long, relatively straight section because the relatively straight section is one of the shortest possible paths between the two volutes 112, 113. Those skilled in the art will realize that the airpath 116 need not be straight at all.

Blowers according to the invention may be designed manually, using prototypes and experimental measurements of air flows and pressures in those prototypes to optimize the design of the airpath 116 and other components. Alternatively, they may be designed, either as a whole or in part, by using computational fluid dynamics computer simulation programs. A variety of computational fluid dynamics programs are known in the art. Computational fluid dynamics programs particularly suited for the design of blowers according to the invention include FLOWORKS (NIKA GmbH, Sottrum, Germany), ANSYS/FLOTRAN (Ansys, Inc., Canonsburg, Pa., USA), and CFX (AEA Technology Engineering Software, Inc., El Dorado Hills, Calif., USA). Such simulation programs give the user the ability to see the effects of airpath design changes on a simulated gas flow.

Many different types of configurations for the two volutes 112, 113 and airpath 116 are possible in a double-ended blower according to the present invention. In general, each volute is designed to retain the gas around the impeller for a short period of time, and to permit a gradual exit of gas into the airpath. The exact configuration of the airpath may depend on many factors, including the configuration of the volutes and the "handedness," or direction of airflow, around each impeller.

The design of the volutes is an art unto itself, as improperly designed volutes may cause a noise, or may interfere with the generation of the desired pressure and flow characteristics. The computational fluid dynamics computer programs described above may also be useful in designing the volutes, although the number of variables involved in volute design usually precludes the volute from being entirely computer-designed.

One common problem with volutes 112, 113 is that they may provide too abrupt of a transition into the airpath 116. An abrupt transition between the volute 112, 113 and the airpath 116 usually leaves a forked path or "lip" around the opening.

When the impeller blades pass by this lip, a noise called "blade passing frequency" is created. Double-ended blowers according to the present invention are particularly suited for use with volutes that are constructed to reduce the occurrence of "blade passing frequency" and other noise.

Figure 6:
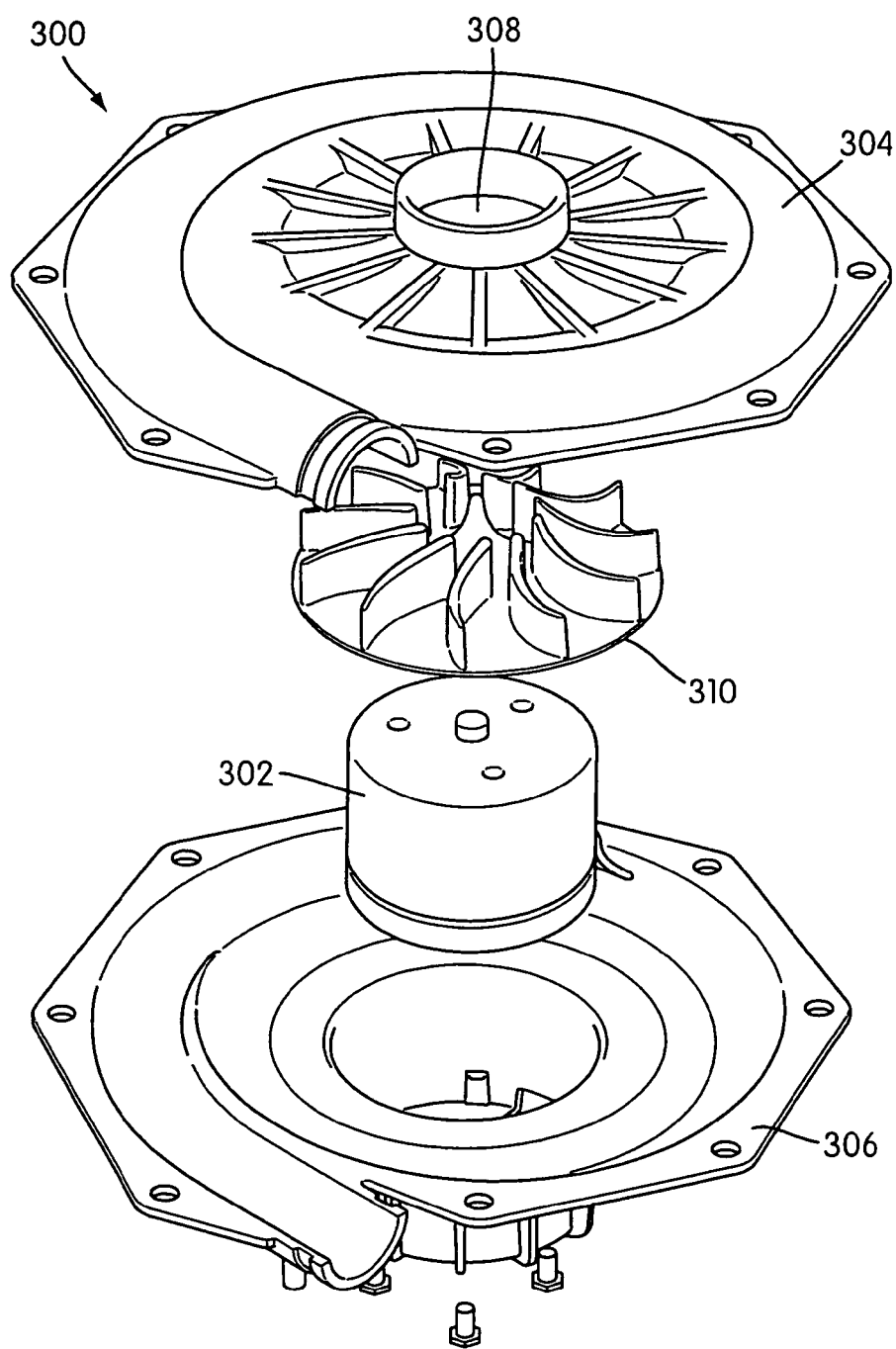
FIG. 6 is a perspective view of an in-plane transitional scroll volute suitable for use in blowers according to the present invention.

FIG. 6 is a perspective view of an in-plane transitional scroll volute 300 suitable for use in a blower according to the present invention. Additionally, the volute 300 may be employed in any conventional blower apparatus. In the view of FIG. 6, the volute 300 is provided with its own motor 302, although it may be adapted for use in a double-ended blower having a single motor driving the impellers in two volutes. As shown, the volute 300 is comprised of two halves 304, 306, the two halves defining upper and lower portions of the volute 300, respectively. The air intake of the volute 308 is located at the center of the top half 304. The two halves 304, 306 define a path which slowly "peels" away from the air rotating with the impeller. In the path defined by the two halves, there is no sudden "lip" or "split" as in conventional volutes, therefore, "blade passing frequency" is reduced or eliminated entirely. The volute 300 depicted in FIG. 6 is particularly suitable for relatively short, wide motors.

Alternatively, any common type of volute may be used, depending on the dimensions of the motor installed in the blower. Another suitable type of volute is the axial volute disclosed in U.S. patent application Ser. No. 09/600,738, filed on Jul. 21, 2000, the contents of which are hereby incorporated by reference herein in their entirety.

One important design consideration for a double-ended blower according to the present invention is the "handedness," or direction of airflow, around each impeller. This "handedness" may be determined by the direction in which the impeller spins, or it may be determined by the orientation and configuration of the individual blades or vanes of the impeller. For example, one impeller may be spun or the blades oriented to drive the air in a clockwise direction, and the other impeller may be spun or the blades oriented to drive the air in a counterclockwise direction, resulting in a "opposing-handed" double-ended blower. Alternatively, both impellers could be driven in the same direction, resulting in a "same-handed" double-ended blower. Blower 100 of FIG. 1 is an example of an "opposite-handed" type of double-ended blower.

A "same-handed" blower is advantageous because the two impellers can be identical, reducing the part count and cost of the blower. However, it should be noted that a designer may choose to design a "same-handed" blower in which the two impellers are each designed and optimized for the air flow in their respective volutes.

An "opposing-handed" blower permits the designer to reduce the length of the shaft on which the impellers are mounted. This may increase the stability of the shaft itself, because it reduces the problems associated with having an imbalance on a long, cantilevered shaft rotating at high speed.

Figure 3:
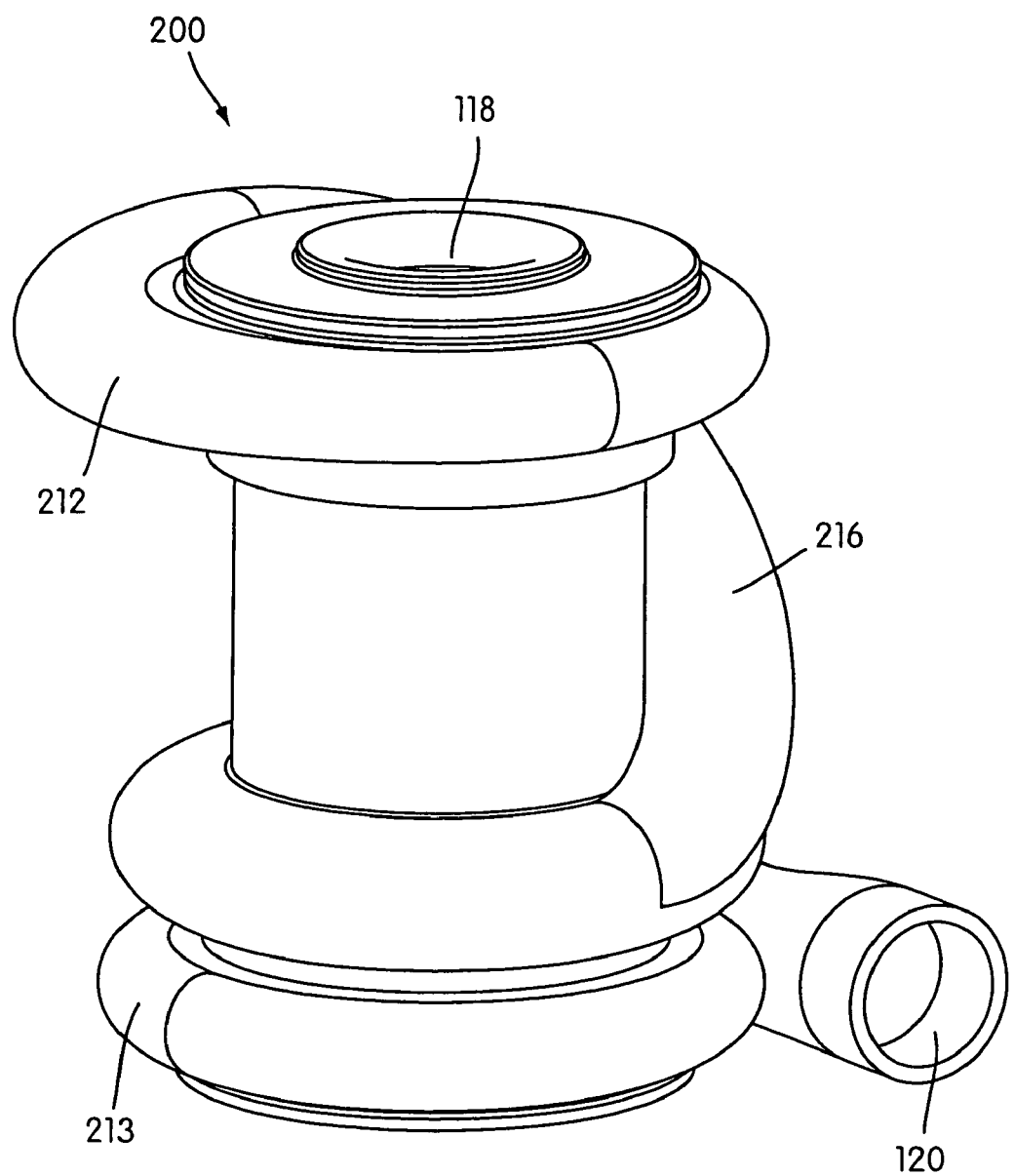
FIG. 3 is a perspective view of a double-ended blower according to a second embodiment of the present invention.

FIG. 3 illustrates a "same-handed" blower 200 according to the present invention. Blower 200 also has two volutes 212, 213, an airpath 216, an air intake 218 and an air outlet 220. As with the embodiments of FIGS. 1 and 2, air is drawn on through intake 118 whereupon the action of the impeller 214 circulates the air in a spiral pattern. However, as is shown in FIG. 3, the airpath 216 between the first and second components has the shape of a helix, i.e., helical. That is, airpath 216 transitions away from the first volute 212 and then slopes downward as it follows the circumference of the blower 200, before bending and gradually fusing with an intake cavity located between the motor 150 and the arcuate flange 160, which defines a second air intake leading to the second impeller. The airflow through the blower 200 is illustrated by the arrows in the perspective view of FIG. 5. The air spirals radially inward when transitioning from the ehlical airpath 216 to the second intake, and once drawn through the second intake, the air is further pressurized and caused to spiral radially outward until reachin outlet conduit 120.

Figure 4:
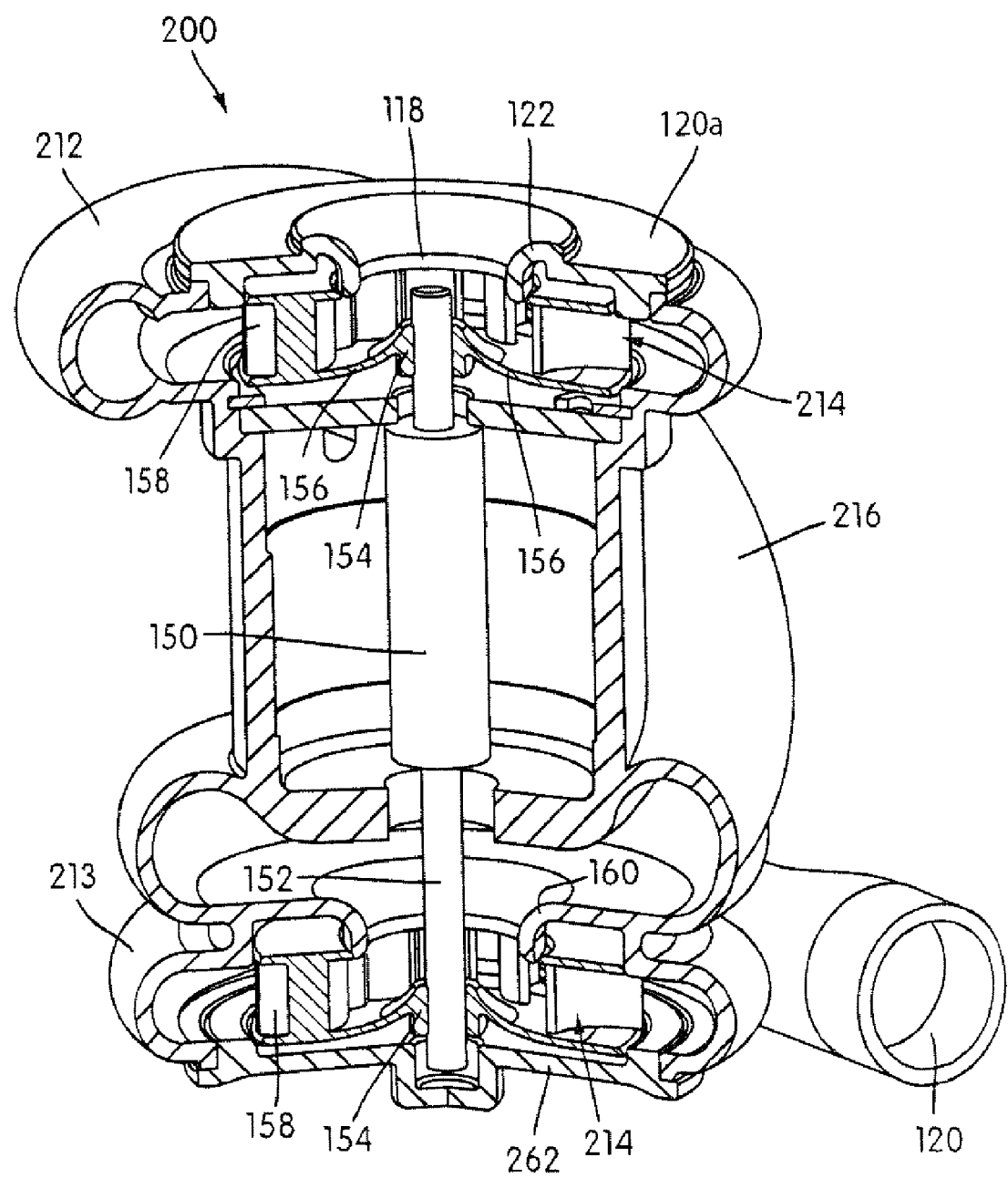
FIG. 4 is a sectional perspective view of the double-ended blower of FIG. 3.

The internal configuration of blower 200 is shown in the partially sectional perspective view of FIG. 4. The internal arrangements of blowers 100 and 200 are substantially similar, and will be described below with respect to components of both blowers, where applicable. As shown in FIG. 4, an electric motor 150 is installed in the center of the blowers 200. Various types of known brackets and mountings may be used to support the motor and to secure it to the interior of the blower 200, although for simplicity, these are not shown in FIG. 4.

The motor 150 drives a single shaft 152. The shaft 152 traverses substantially the entire length of the blower 100, 200 along its center, and is secured to an impeller 114, 115, 214 at each end. The shaft may be round, square, keyed, or otherwise shaped to transmit power to the two impellers 114, 115, 214. The connection between the impellers 114, 115, 214 and the shaft 152 may be created by an interference fit between the two parts, a weld, an adhesive, or fasteners, such as set screws. In blowers 100 and 200, the connection between the shaft 152 and the impellers 114, 115, 214 is by means of a vertically oriented (i.e., oriented along the axis of the shaft 152) annular flange 154 formed in the center of the impellers 114, 115, 214. In FIGS. 3 and 4, the connection between the impellers 114, 115, 214 and the shaft is shown as an interference fit.

The impeller 114, 115, 214 is substantially annular in shape. The center section 156 of the impeller 114, 115, 214, is a thin plate which extends radially outward from the shaft 152 to the blades 158, and is upswept, gradually curving downward as it extends outward from the shaft 152 towards the blades 158. The actual diameter of each impeller 114, 115, 214 may be smaller than that of a conventional blower with a single impeller. Fast pressure rise time in a blower requires a low rotational inertia, which varies as the diameter to the fourth power. Because impellers 114 and 214 of blowers 100 and 200 are smaller in diameter, they have less rotational inertia, and thus, are able to provide a faster pressure rise time. In addition to diameter, other design parameters of the impellers 114, 214 may be modified to achieve a lower rotational inertia. Other techniques to reduce rotational inertia include "scalloping" the shrouds to produce a "starfish-shaped" impeller, using an internal rotor motor, and using materials, such as liquid crystal polymer, that can be molded into thinner wall sections, so that impeller blades can be hollowed out and strengthened by ribs.

Figure 5:
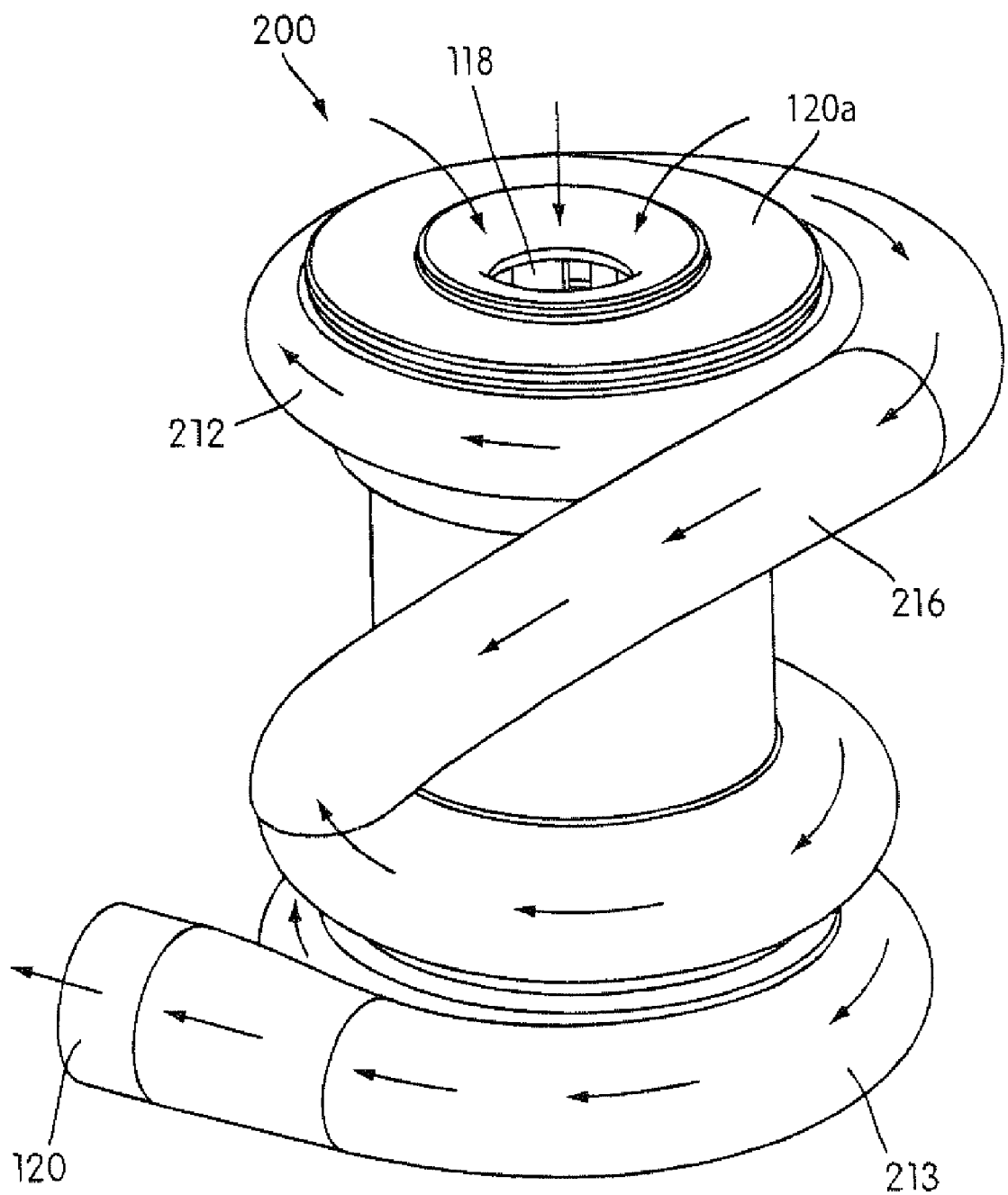
FIG. 5 is a rear perspective view of the double-ended blower of FIG. 3, illustrating the flow therethrough.

Referring to FIGS. 4 and 5, which show the same-handed, double-ended blower, the top of the first volute 212 is open, forming the air intake 118. At the air intake 118, the top surface 120a of the blower 100 curves arcuately inward, forming a lip 122 over the top of the impeller 214. The upswept shape of the impeller center section 156 and the lip 122 of the top surface 120a confine the incoming air to the blower volume inside the first volute 212 and help to prevent air leakage during operation. An arcuate flange 160 similar to the arcuate top surface 120a extends from the lower interior surface of the blower 200, forming the top of the second volute 213. A contoured bottom plate 162, 262 forms the bottom of the second volute 113, 213 of each blower 100, 200. The bottom plate 162 of blower 100 has a hole in its center, allowing the airpath 116 to enter, while the bottom plate 262 of blower 200 has no such hole. As described above, the arcuate flange 160 acts as the air intake for the second volute 213 of blower 200. In blower 200, stator vanes and additional flow shaping components may be added to the cavity between the motor 150 and the arcuate flange 160 to assist in distributing the incoming air so that it enters the second volute 213 from all sides, rather than preferentially from one side.

As is evident from FIGS. 2 and 4, blowers according to the present invention may have many intricate and contoured surfaces. Such contours are used, as in the case of the arcuate top surface 120a and arcuate flange 160, to direct gas flow and prevent gas leakage. The no-leak requirement is particularly important when the gas flowing through the blower 100, 200 has a high concentration of oxygen gas. If high-concentration oxygen is used, gas leakage may pose a safety hazard. Also, apart from any safety considerations, leaking gas may produce unwanted noise, and may reduce blower performance.

The number of intricate, contoured surfaces present in blowers according to the present invention makes a production method such as investment casting particularly suitable. Although relatively expensive, investment casting can produce a single part with many hidden and re-entrant features, whereas other methods of production may require that a design be split into many parts to achieve equivalent function. However, a large number of parts is generally undesirable—in order to minimize the potential for gas leaks, the number of parts is best kept to a minimum and the number of joints between parts is also best kept to a minimum.

There are also a number of materials considerations for blowers according to the present invention. Metals are typically used in investment casting, but some metals are particularly sensitive to oxidation, which is a concern because medical grade oxygen gas may be used in blowers according to the present invention. One particularly suitable material for the blowers 100, 200 is aluminum. Whereas steel may rust on exposure to high concentrations of oxygen, aluminum oxidizes quickly, the oxide forming an impervious seal over the metal. Whichever metal or other material is used, it is also important that the material has a high thermal conductivity and is able to draw heat away from the airpath, to prevent any heat-related ignition of oxygen.

While the use of aluminum has many advantages, it does have a tendency to "ring," or resonate, during blower operation. Therefore, damping materials may be installed in an aluminum blower to reduce the intensity of the vibration of the aluminum components.

In blowers 100 and 200, the electric motor 150 is driven at variable speeds to achieve the desired IPAP and EPAP pressures. The double-ended (i.e., two-stage) design of the blowers means that the range of motor speeds traversed to achieve the two pressures is reduced. The narrower range of motor speeds results in a faster pressure response time than that provided by a single-stage blower having similar motor power and drive characteristics. In addition, the narrower variation in speed applies less stress to the rotating system components, resulting in increased reliability with less acoustic noise.

The performance of blowers 100 and 200 is approximately equal to the combined performance of the two impeller/volute combinations, minus the pressure/flow curve of the airpath 116, 216 between the two volutes 112, 113, 212, 213. For a variety of reasons that are well known in the art, the actual performance of the blowers 100, 200 will depend upon the instantaneous flow rate of the particular blower 100, 200, as well as a number of factors. At higher flow rates, the pressure drop in the airpath 116, 216 is generally more significant.

Double-ended blowers according to the present invention may be placed in a CPAP apparatus in the same manner as a conventional blower. The blower is typically mounted on springs, or another shock-absorbing structure, to reduce vibrations.

A Further Embodiment

Figure 7:
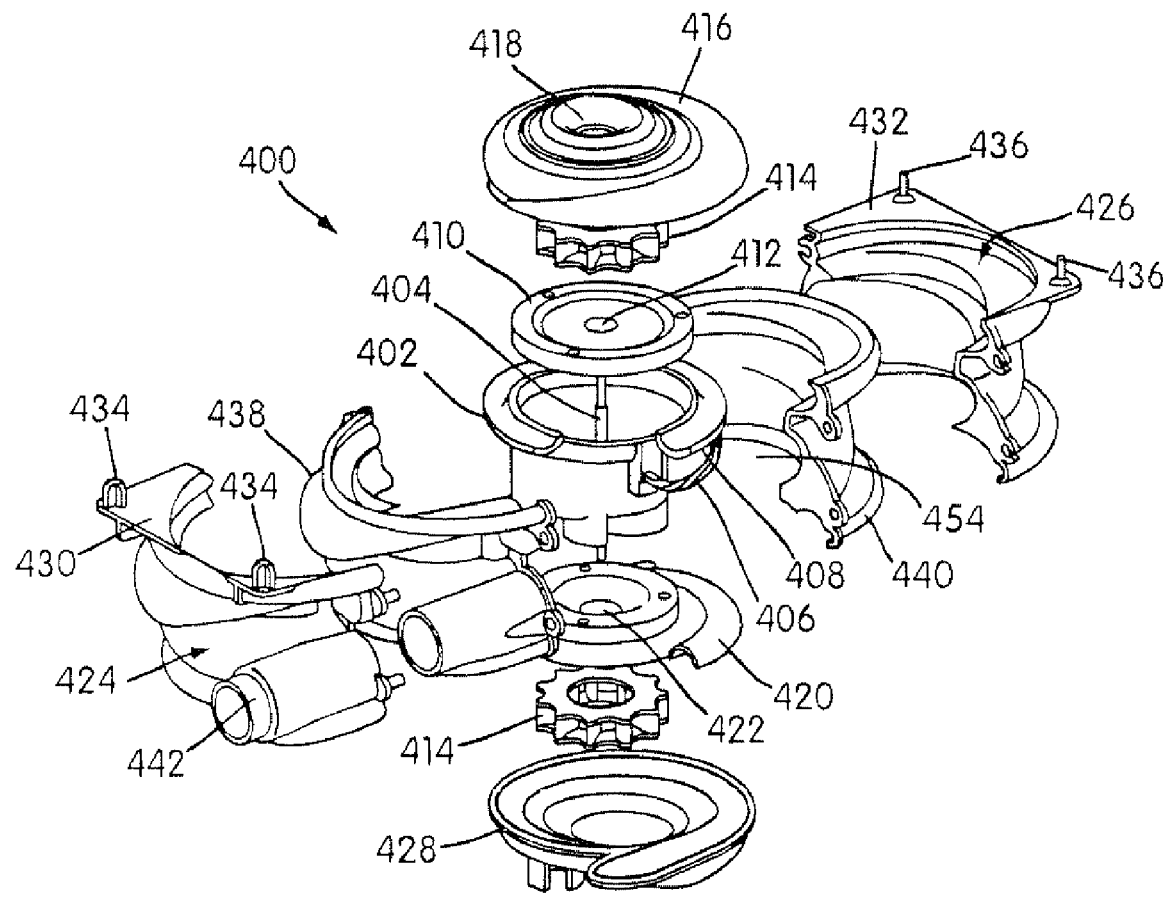
FIG. 7 is an exploded perspective view of a double-ended blower according to another embodiment of the present invention.

One further embodiment of the present invention is illustrated in FIG. 7, an exploded perspective view of a double-ended blower 400 according to the present invention. The motor and stator blade portion 402, located in the center of the exploded view, is investment cast from aluminum in this embodiment, although other manufacturing methods are possible and will be described below. The aluminum, as a good conductor of heat, facilitates the dissipation of heat generated by the accelerating and decelerating motor. Each end of the shaft 404 is shown in FIG. 7, but the motor windings, bearing and cover are not shown. The motor power cord 406 protrudes from the motor and stator blade portion 402 and exits the blower 400 through a sealed orifice 450. The motor and stator blade portion 402 includes, at its top, a bottom portion of the upper volute 408.

As a variation of the design illustrated in FIG. 7, the motor and stator blade portion 402 may be made separately from the bottom portion of the upper volute 408. If the two components are made separately, investment casting would not be required. For example, the motor body may be die cast, while the bottom portion of the upper volute 408 may be injection molded.

Secured to the motor and stator blade portion 402 by bolts or other fasteners is a circular plate 410, in which a hole 412 is provided for the passage of the shaft 404. An impeller 414 rests atop the circular plate. The impeller 414 is scalloped along its circumference to reduce its rotational inertia, giving it a "starfish" look.

An upper endcap 416 is secured above the impeller 414, and provides the top portion of the upper volute. The upper and lower volutes in this embodiment are versions of the in-plane transitional scroll volute 300 illustrated in FIG. 6. An aperture 418 in the center of the upper endcap 416 serves as the air intake of the blower 400.

On the lower end of the blower 400, a contoured plate 420 forms the top portion of the lower volute. The top of the contoured plate 420 is raised and curves arcuately downward toward a hole 422. As was explained above, the contoured plate 420 helps to shape the airflow and to ensure that it enters the impeller cavity from all sides, rather than preferentially from a single direction. Beneath the contoured plate 420, a lower impeller 414 rotates proximate to a lower endcap 428. The two endcaps, 416, 428 may be die cast (e.g., from aluminum or magnesium alloy) or they may be injection molded from an appropriate metal.

The airpath 454 between the upper and lower volutes is an integral part of the left 424 and right 426 side casings, onto which the other components are secured. The left side casing 424 also provides the air outlet 442 for the blower 400. The left 424 and right 426 side casings are secured together with bolts or other removable fasteners. On the top surface of the side casings 424, 426 are square flanges 430, 432 having protrusions 434, 436 that allow the blower 400 to be mounted on springs inside a CPAP apparatus. In FIG. 7, the protrusions 434, 436 are shown as having different sizes and shapes, however, in FIGS. 8 and 9, the protrusions 434 are shown as having the same shape. It will be realized that the protrusions 434, 436 may take either of the depicted shapes, or any other shape, depending on the properties and arrangement of the springs onto which the blower 400 is mounted.

The double-ended blower 400 also includes two damping sleeves 438, 440. The damping sleeves 438, 440 are rubber or foam rubber components that are injection molded to match the internal contours of the left 424 and right 426 side casings, respectively. In one implementation, the damping sleeves 438, 440 are 40 Shore A hardness polyurethane formed from a rapid prototype silicone mold. Alternatively, the damping sleeves 438, 440 could be silicone, or another elastomer that is stable at the high temperatures generated by the motor.

The damping sleeves 438, 440 serve three major purposes in blower 400: they form the actual airpath 454, they provide a seal between the other components, and they dampen the vibrations of the other parts. The rubber or foam rubber material of the damping sleeves 438, 440 is particularly suitable for the airpath 454, as it allows for re-entrant molds (i.e., undercuts). The damping properties of the damping sleeves 438, 440 reduce the "ringing" of the aluminum components that would otherwise be experienced.

Figure 8:
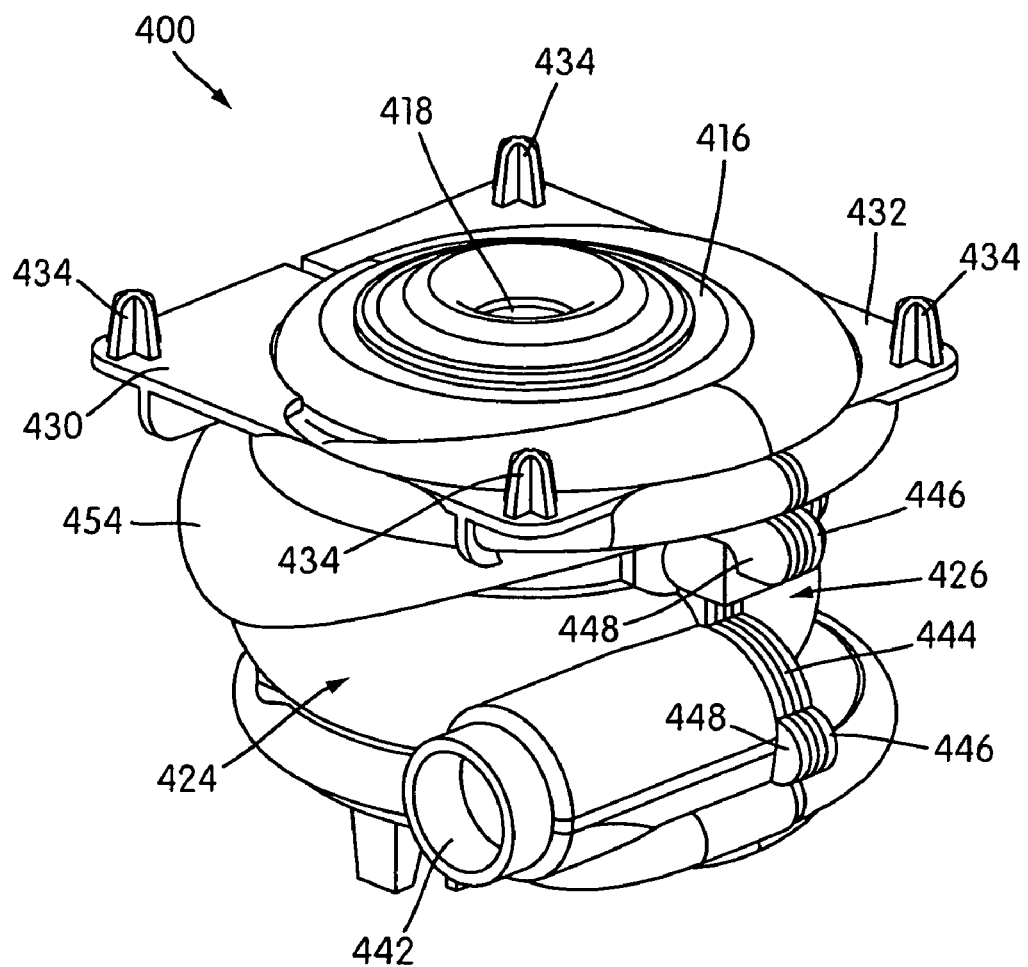
FIG. 8 is an assembled perspective view of the double-ended blower of FIG. 7 from one side.
Figure 9:
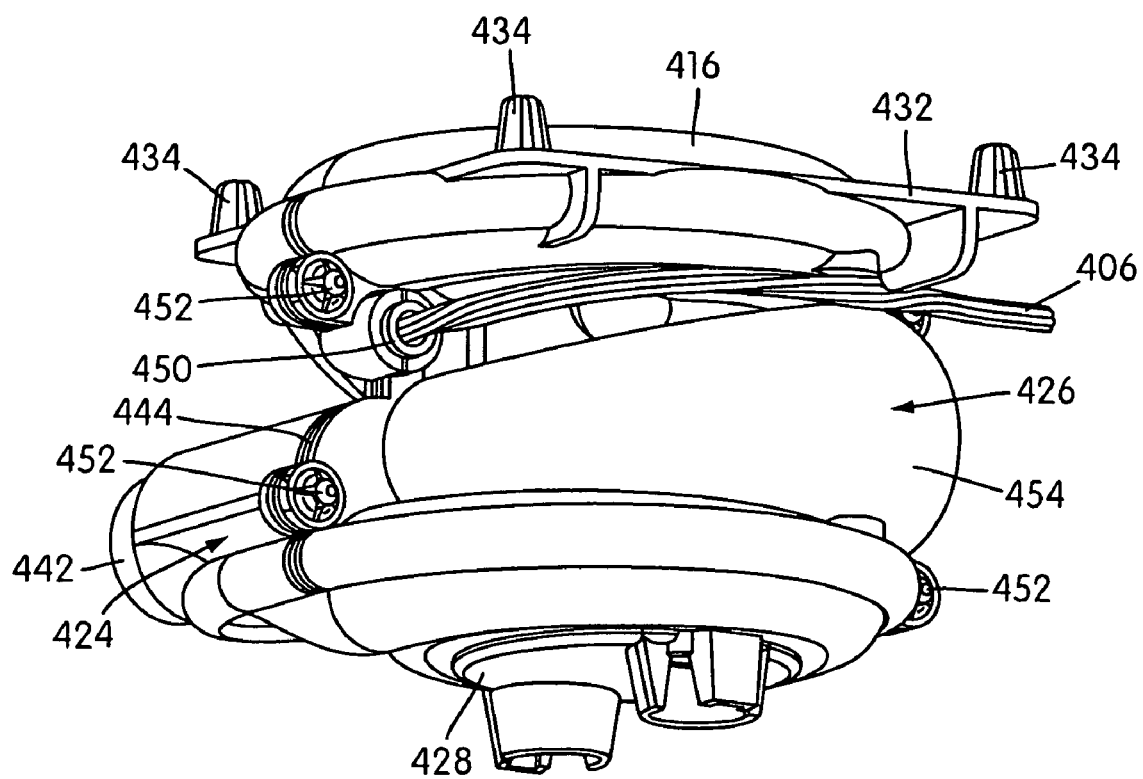
FIG. 9 is an assembled perspective view of the double-ended blower of FIG. 7 from another side.

FIG. 8 is an assembled perspective view of blower 400 from one side. The assembled air outlet 442 is shown in FIG. 8, as is the seam 444 between the left 424 and right 426 side casings. As shown in FIG. 8, and in the rotated perspective view of FIG. 9, flanges 446, 448 protrude laterally from the edge of each side casing 424, 426 and abut to form the seam 444. The two side casings 424, 426 are secured together by bolts 452 that pass through the flange 446 provided in the right side casing 426 and into threaded holes provided in the flange 448 of the left side casing 424.

Blower 400 has several advantages. First, investment casting is not required to produce blower 400, which reduces the cost of the blower. Additionally, because the components of blower 400 have fewer hidden and intricate parts, the castings can be inspected and cleaned easily. Finally, blower 400 is easier to assemble than the other embodiments because the components are clamped together using the two side casings 424, 426, which can be done with simple fasteners.

While the invention has been described by way of example embodiments, it is understood that the words which have been used herein are words of description, rather than words of limitation. Changes may be made without departing from the scope and spirit of the invention in its broader aspects. Although the invention has been described herein with reference to particular embodiments, it is understood that the invention is not limited to the particulars disclosed. The invention extends to all appropriate equivalent structures, uses and mechanisms.

What is claimed is:

1. A CPAP/NIPPV apparatus for delivering breathable gas to a human patient including a double-ended blower comprising:
   a motor supporting first and second shaft ends extending from opposite ends of the motor;
   a first impeller attached to the first shaft end, the first impeller having a first air intake and a first volute;
   a second impeller attached to the second shaft end, the second impeller having a second air intake and a second volute; and
   a casing to support and enclose the motor thereby enabling establishment of an air flow channel within the casing and surrounding the motor to guide air along an air path from the first impeller to the second impeller, wherein the air flow channel is constructed and arranged so that at least part of the air path between the first and second volutes is helical, said casing formed with an outlet downstream of the second impeller.

2. A CPAP/NIPPV apparatus as claimed in claim 1, wherein the casing includes first and second halves bisected along a plane parallel to an axis extending along said first and second shaft ends, said first and second halves being fastened to one another.

3. A CPAP/NIPPV apparatus as claimed in claim 1, further comprising a damping sleeve provided to the casing.

4. A CPAP/NIPPV apparatus as claimed in claim 3, wherein the damping sleeve includes separable first and second halves that define in part the air flow channel radially between the motor and the damping sleeve when combined.

5. A CPAP/NIPPV apparatus as claimed in claim 3, wherein the damping sleeve is made of at least one of silicone, foam, rubber and polyurethane.

6. A CPAP/NIPPV apparatus as claimed in claim 1, wherein the second air intake is positioned between the first and second impellers.

7. A CPAP/NIPPV apparatus as claimed in claim 1, wherein each impeller has scalloped edges.

8. A CPAP/NIPPV apparatus as claimed in claim 1, wherein the first impeller is configured for rotation within the first volute defined adjacent a first end of the casing.

9. A CPAP/NPPV apparatus as claimed in claim 8, wherein a first endcap and a portion of a motor stator of the motor define the first volute.

10. A CPAP/NIPPV apparatus as claimed in claim 1, further comprising a first endcap adjacent the first impeller and a second endcap adjacent the second impeller, wherein said air flow channel is defined between the first and second endcaps.

11. A CPAP/NIPPV apparatus as claimed in claim 10, wherein the first endcap includes the first air intake leading to the first impeller.

12. A CPAP/NIPPV apparatus as claimed in claim 4, wherein the casing includes an outlet to direct the gas along a path that is substantially tangential to the second impeller.

13. A CPAP/NIPPV apparatus as claimed in claim 1, wherein the second impeller is configured for rotation within the second volute defined adjacent a second end of the casing.

14. A CPAP/NIPPV apparatus as claimed in claim 13, wherein the second volute is defined between a contoured plate provided to a stator of the motor and an inside surface of a second end cap, the contoured plate including the second air intake.

15. A CPAP/NIPPV apparatus as claimed in claim 1, wherein the casing is made of aluminum.

16. A CPAP/NIPPV apparatus as claimed in claim 1, wherein the first and second shaft ends are provided as part of a common shaft.

17. A CPAP/NIPPV apparatus as claimed in claim 1, wherein both impellers are configured for rotation in the same direction.

18. A CPAP/NIPPV apparatus as claimed in claim 1, wherein the first and second impellers are configured for rotation in opposite directions.

19. A CPAP/NIPPV apparatus as claimed in claim 1, wherein the first and second impellers have blades configured to direct the air in a common direction.

20. A CPAP/NIPPV apparatus including a double-ended blower comprising:
   a motor supporting opposed first and second shaft ends;
   a first impeller provided to the first shaft end, the first impeller having a first air intake;
   a second impeller provided to the second shaft end, the second impeller having a second air intake; and
   a casing to support and enclose the motor thereby enabling establishment of an air path radially between the motor and the casing to guide air from the first impeller to the second impeller, wherein the air path includes a first path portion adjacent the first impeller with a spiral component, a second path portion between the first and second impellers with a helical component, and a third path portion adjacent the second impeller with a spiral component and a radial component, and wherein the CPAP/NIPPV apparatus is pre-set to deliver inspiratory positive airway pressure (IPAP) during the inspiratory phase of the patient's breathing cycle, and to deliver expiratory positive airway pressure (EPAP) during the expiration phase of the patient's respiratory cycle.

21. A CPAP/NIPPV apparatus as claimed in claim 20, wherein the first and second impellers have blades configured to direct the air in opposite directions.

22. A CPAP/NIPPV apparatus as claimed in claim 20, further comprising a patient interface.

23. A CPAP/NIPPV apparatus as claimed in claim 20, wherein the IPAP is greater than the EPAP.

24. A CPAP/NIPPV apparatus as claimed in claim 20, wherein the blower is configured to generate pressures in the range of about 4 cm H2O to 28 cm H2O at flow rates of up to of about 180 L/min as measured at the patient interface.

25. A Continuous Positive Airway Pressure/Noninvasive Positive Pressure Ventilation (CPAP/NIPPV) apparatus for treatment of a patient with a sleeping disorder, the apparatus including:
    a gas flow path between a gas inlet and a gas outlet;
    a motor;
    an impeller assembly, the impeller assembly including
        a shaft in communication with said motor for rotational motion about a first axis; and
        first and second impellers fixedly secured to said shaft;
    wherein said first and second impellers are placed in fluid communication with one another by said gas flow path such that both impellers are disposed between said gas inlet and said gas outlet to cooperatively pressurize gas flowing from said gas inlet to said gas outlet; and
    an elastomeric sleeve disposed around the first and second impellers and the motor and defining a portion of the gas path that extends radially between the motor and the elastomeric sleeve from the first impeller to the second impeller.

26. A CPAP/NIPPV apparatus of claim 25, wherein said first and second impellers are disposed at opposite ends, respectively, of said motor.

27. A CPAP/NIPPV apparatus as claimed in claim 25, wherein an internal surface of the elastomeric sleeve is formed adjacent a motor stator of the motor so as to define the gas path between the motor stator and the internal surface.

28. A CPAP/NIPPV apparatus as claimed in claim 25, further comprising a housing provided to and surrounding the sleeve.

29. A CPAP/NIPPV apparatus as claimed in claim 28, wherein the sleeve and/or housing comprises first and second halves.

30. A CPAP/NIPPV apparatus of claim 29, wherein the first and second halves of the sleeve are bisected in a plane parallel to the axis of the shaft.

31. A CPAP/NIPPV apparatus as claimed in claim 28, wherein the housing is made of aluminum.

32. A CPAP/NIPPV apparatus as claimed in claim 25, wherein the sleeve is made of silicone, foam, rubber and/or polyurethane.

33. A CPAP/NIPPV apparatus as claimed in claim 25, wherein the gas path is defined in part by a helical path from the first impeller to the second impeller.

34. A CPAP/NIPPV apparatus as claimed in claim 25, further comprising an endcap adjacent the first impeller, wherein the endcap includes an intake for the first impeller in the form of a central inlet aperture.

35. A CPAP/NIPPV apparatus as claimed in claim 34, wherein the endcap and a portion of a motor stator of the motor define a volute for the first impeller.

36. A CPAP/NIPPV apparatus as claimed in claim 25, further comprising a patient interface, such as a mask.

37. A CPAP/NIPPV apparatus as claimed in claim 25, wherein the CPAP/NIPPV apparatus is pre-set to deliver inspiratory positive airway pressure (IPAP) during the inspiratory phase of the patient's breathing cycle, and to delivery expiratory positive airway pressure (EPAP) during the expiration of the patient's respiratory cycle.

38. A CPAP/NIPPV apparatus as claimed in claim 37, wherein the IPAP is greater than the EPAP.

39. A CPAP/NIPPV apparatus as claimed in claim 25, wherein the blower is configured to generate pressures in the range of about 4 cm H2O to 28 cm H2O at flow rates of up to about 180 L/min as measured at a patient interface.

40. A CPAP/NIPPV apparatus as claimed in claim 25, wherein each impeller comprises scalloped edges.

41. A CPAP/NIPPV apparatus as claimed in claim 25, wherein said portion of the gas path that extends between the first and second impellers is at least partially helical.

42. A CPAP/NIPPV apparatus of claim 25, wherein sleeve extends from an inlet of the first impeller to an intake of the second impeller.

43. A CPAP/NIPPV apparatus for treatment of a patient with a sleeping disorder, including the blower as claimed in claim 1.

* * * * *